US006921536B2

(12) United States Patent
Jacobs et al.

(10) Patent No.: US 6,921,536 B2
(45) Date of Patent: Jul. 26, 2005

(54) *LAWSONIA INTRACELLULARIS* VACCINE

(75) Inventors: Antonius Arnoldus Christiaan Jacobs, Kessel (NL); Paul Vermeij, St. Anthonis (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/034,500

(22) Filed: Dec. 20, 2001

(65) Prior Publication Data

US 2005/0069559 A1 Mar. 31, 2005

(30) Foreign Application Priority Data

Dec. 20, 2000 (EP) .............................................. 00204660

(51) Int. Cl.$^7$ ....................... A61K 39/02; A61K 39/00; C07K 1/00; C07H 21/04
(52) U.S. Cl. ................................ 424/234.1; 424/190.1; 424/185.1; 424/184.1; 536/23.1; 536/23.7; 435/69.7; 435/69.3; 435/69.1; 530/300; 530/350
(58) Field of Search ........................... 424/234.1, 190.1, 424/185.1, 184.1; 536/23.1, 23.7; 435/69.7, 69.3, 69.1; 530/350, 300

(56) References Cited

U.S. PATENT DOCUMENTS

| | | | |
|---|---|---|---|
| 5,610,059 | A | 3/1997 | Joens et al. |
| 5,714,375 | A | 2/1998 | Knittel et al. |
| 5,885,823 | A | 3/1999 | Knittel et al. |

FOREIGN PATENT DOCUMENTS

| | | |
|---|---|---|
| JP | 2001169787 | 10/1999 |
| WO | 9304163 | 3/1993 |
| WO | 9639629 | 12/1996 |
| WO | 97 20050 A | 6/1997 |
| WO | 0069903 | 5/1999 |
| WO | 0069904 | 5/1999 |
| WO | 0069906 | 5/1999 |
| WO | 00 69905 A | 11/2000 |

OTHER PUBLICATIONS

McOrist, S., Biod, R. and Lawson, G. H. K. 1989. Infect. Immun. 57: 957–962.*
Smith et al 2000Infection and Immunity, Dec. 2000, pp. 6737–6743, vol. 68, No. 12.*
Ellis, R.W. (Chapter 29 of "VACCINES" Plotkin, 5.A. et al. (eds) published by W. B. Saunders company (Philadelphia) in 1988, especially p. 571.*
Rudinger et al, in "Peptide Hormones", edited by Parsons, J.A., University Park Press, Jun. 1976, p. 6.*
Burgess et al., The Journal of Cell Biology, 111:2129–2138, 1990.*
Lazar et al., Molecular and Cellular Biology, 8(3): 1247–1252, 1988.*
Jobling et al. (Mol. Microbiol, 1991, 5(7): 1755–67.*
McCluskey et al, Infect Immun Jun. 2002; 70(6): 2899–907.*
McOrist, S., et al: "Infection and Immunity." vol. 61, (1993) No. 10, 5237–5244.
McOrist, S., et al: "Infection and Immunity." vol. 60, (1992) No. 10, 4184–4191.
Herrick, J.B.: "Large Anim. Pract." vol. 19, (1998) No. 6, 15.
Lawson, G.H. et al: "Vet. Rec." vol. 107, (1980) No. 18, 424–425.
Holyoake, P.K., et al: "J. Clin. Microbiol." vol. 32, (1994) No. 8, 1980–1985.
Database Swall 'Online!, Oct. 1, 2000, retrieved from EBI Database accession No. Q9KQE0.
Database Swall 'Online!, May 1, 1999, retrieved from EBI Database accession No. Q9ZCH2.
Kim J et al: Immunohistochemistry and Polymerase Chain Reaction for the Detection of *Lawsonia intracellularis* in Porcine Intentinal Tissues with Proliferative Enteropathy; Journal of Veterinary Medical Science; vol. 7, No. 62, Jul. 2000, pp. 771–773.
Dale C Jane H et al: "Identification and sequencing of the groE operon and flanking genes of *Lawsonia intracellularis*: Use in phylogeny", Microbiology, Society for General Microbiology, Reading, GB, vol. 144, No. 8, Aug. 1998, pp. 2073–2084.

* cited by examiner

*Primary Examiner*—Patricia A. Duffy
*Assistant Examiner*—Padma Baskar
(74) *Attorney, Agent, or Firm*—William H. Blackstone

(57) ABSTRACT

The present invention relates i.a. to nucleic acid sequences encoding novel *Lawsonia intracellularis* proteins. It furthermore relates to DNA fragments, recombinant DNA molecules and live recombinant carriers comprising these sequences. Also it relates to host cells comprising such nucleic acid sequences, DNA fragments, recombinant DNA molecules and live recombinant carriers. Moreover, the invention relates to proteins encoded by these nucleotide sequences. The invention also relates to vaccines for combating *Lawsonia intracellularis* infections and methods for the preparation thereof. Finally the invention relates to diagnostic tests for the detection of *Lawsonia intracellularis* DNA, the detection of *Lawsonia intracellularis* antigens and of antibodies against *Lawsonia intracellularis*.

5 Claims, 2 Drawing Sheets

LAWSONIA INTRACELLULARIS VACCINE

The present invention relates to nucleic acid sequences encoding novel *Lawsonia intracellularis* proteins, to DNA fragments, recombinant DNA molecules and live recombinant carriers comprising these sequences, to host cells comprising such nucleic acid sequences, DNA fragments, recombinant DNA molecules and live recombinant carriers, to the proteins encoded by these nucleotide sequences, to vaccines for combating *Lawsonia intracellularis* infections and methods for the preparation thereof, and to diagnostic tools for the detection of *Lawsonia intracellularis*.

BACKGROUND OF THE INVENTION

Porcine proliferative enteropathy (PPE or PE) has become an important disease of the modern pig industry world-wide. The disease affects 15% to 50% of the growing herds and up to 30% of the individual animals in established problem herds. Today annual economical losses have been estimated US$ 5–10 in extra feed and facility time costs per affected pig. PPE is a group of chronic and acute conditions of widely differing clinical signs (death, pale and anaemic animals, watery, dark or bright red diarrhoea, depression, reduced appetite and reluctance to move, retarded growth and increased FCR). However there are two consistent features. The first, a pathological change only visible at necropsy, is a thickening of the small intestine and colon mucosa. The second is the occurrence of intracytoplasmatic small-curved bacteria in the enterocytes of the affected intestine. These bacteria have now been established as the etiological agent of PPE and have been name *Lawsonia intracellularis*.

Over the years *Lawsonia intracellularis* has been found to affect virtually all animals including monkeys, rabbits, ferrets, hamsters, fox, horses, and other animals as diverse as ostrich and emoe. *Lawsonia intracellularis* is a gram-negative, flagellated bacterium that multiplies in-eukaryotic enterocytes only and no cell-free culture has been described. In order to persist and multiply in the cell *Lawsonia intracellularis* must penetrate dividing crypt cells. The bacterium associates with the cell membrane and quickly enters the enterocyte via an entry vacuole. This then rapidly breaks down (within 3 hours) and the bacteria flourish and multiply freely in the cytoplasm. The mechanisms by which the bacteria cause infected cells to fail to mature, continue to undergo mitosis and form hypoplastic crypt cells is not yet understood.

The current understanding of *Lawsonia intracellularis* infection, treatment and control of the disease has been hampered by the fact that *Lawsonia intracellularis* can not be cultivated in cell-free media. Although there are reports of successful co-culturing *Lawsonia intracellularis* in rat enterocytes this has not lead to the development of vaccines for combating *Lawsonia intracellularis*, although there clearly is a need for such vaccines.

SUMMARY OF THE INVENTION

It was surprisingly found now, that *Lawsonia intracellularis* produces three novel outer membrane proteins (OMPs) that, alone or in combination, are capable of inducing protective immunity against *Lawsonia intracellularis*.

The three novel outer membrane proteins will be referred to as the 19/21 kD, 37 kD and 50 kD protein. The 19/21 kD protein is found in two different forms, a 19 kD form and a 21 kD form, one protein being a modified form of the other and both comprising an identical amino acid sequence.

The amino acid sequences of the 37 kD and 50 kD protein are presented in sequence identifiers SEQ ID NO: 2 and 4.

The genes encoding these two proteins have been sequenced and their nucleic acid sequence is shown in sequence identifiers SEQ ID NO: 1 and 3. The 19/21 kD protein is characterised by three internal amino acid sequences of respectively 7, 12 and 12 amino acids. These amino acid sequences are presented in SEQ ID NO: 5, 6 and 7.

Figure 1:
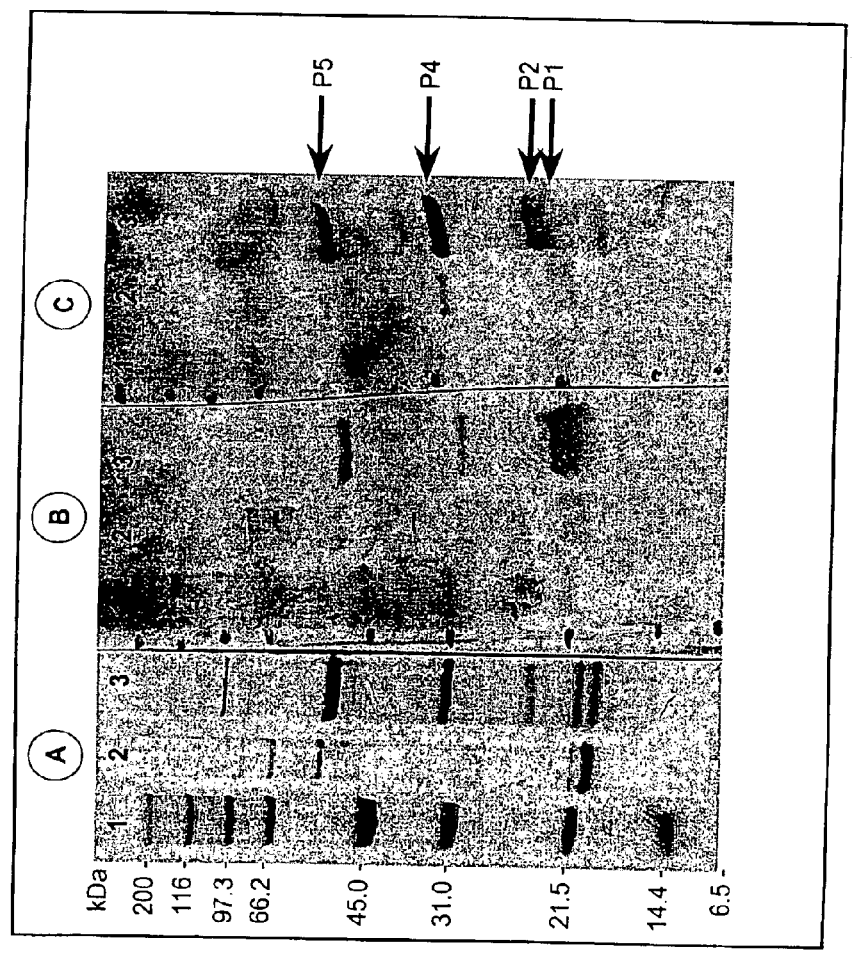
FIG. 1. SDS-PAGE gel electrophoresis and immunoblots of *L. intracellularis* whole cells and *L. intracellularis* outer membrane preparation probed with rabbit antisera. Lanes: 1, Prestained precision markers (BioRad); 2, *L. intracellularis* total cell extract; 3, *L. Intracellularis* outer membrane preparation. Panels: A: protein visualization with Coomassie brilliant blue, B: blot probed with serum raised against purified outer membrane proteins (R279); C, blot probed with serum raised against whole cells (R291). The 19/21 kD, 37 kD and 50 kD protein are indicated with P1/P2, P4 and P5 respectively.

It is well-known in the art, that many different nucleic acid sequences can encode one and the same protein. This phenomenon is commonly known as wobble in the second and especially the third base of each triplet encoding an amino acid. This phenomenon can result in a heterology of about 30% for two nucleic acid sequences still encoding the same protein. Phenomenon. Therefore, two nucleic acid sequences having a sequence homology of about 70% can still encode one and the same protein.

Thus, one embodiment relates to nucleic acid sequences encoding a *Lawsonia intracellularis* protein and to parts of that nucleic acid sequence that encode an immunogenic fragment of that protein, wherein those nucleic acid sequences or parts thereof have a level of homology with the nucleic acid sequence of SEQ ID NO: 1 of at least 70%.

Preferably, the nucleic acid sequence encoding this *Lawsonia intracellularis* protein or the part of said nucleic acid sequence has at least 80%, preferably 90%, more preferably 95% homology with the nucleic acid sequence of SEQ ID NO: 1. Even more preferred is a homology level of 98% or even 100%.

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 3 of at least 70%.

Preferably, the nucleic acid sequence encoding this *Lawsonia intracellularis* protein or the part of said nucleic acid sequence has at least 80%, preferably 90%, more preferably 95% homology with the nucleic acid sequence of SEQ ID NO: 3. Even more preferred is a homology level of 98% or even 100%.

The level of nucleotide homology can be determined with the computer program "BLAST 2 SEQUENCES" by selecting sub-program: "BLASTN."

A reference for this program is Tatiana A. Tatusova, Thomas L. Madden FEMS Microbiol. Letters 174: 247–250 (1999). Parameters used are the default parameters:

Reward for a match: +1. Penalty for a mismatch: −2. Open gap: 5. Extension gap: 2. Gap x_dropoff: 50.

Also, one form of this embodiment of the invention relates to nucleic acid sequences encoding a novel *Lawsonia intracellularis* protein comprising an amino acid sequence as depicted in SEQ ID NO: 2, or an immunogenic fragment of that polypeptide.

In a preferred form of that embodiment, that nucleic acid sequence has a homology of at least 90%, more preferably 95%, 98% or even 100% with the nucleic acid sequence as depicted in SEQ ID NO: 1.

Also, one form of this embodiment of the invention relates to nucleic acid sequences encoding a novel *Lawsonia intracellularis* protein having an amino acid sequence as depicted in SEQ ID NO: 4, or an immunogenic fragment of said polypeptide.

In a preferred form of that embodiment, that nucleic acid sequence has a homology of at least 90, more preferably 95%, 98% or even 100% % with the nucleic acid sequence as depicted in SEQ ID NO: 3.

Since the present invention discloses nucleic acid sequences encoding novel *Lawsonia intracellularis* 37 kD and 50 kD proteins, it is now for the first time possible to obtain these proteins in sufficient quantities. This can e.g. be done by using expression systems to express the genes encoding the proteins.

Therefore, in a more preferred embodiment, the invention relates to DNA fragments comprising a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment or a nucleic acid sequence according to the invention that is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6). Functionally linked promoters are promoters that are capable of controlling the transcription of the nucleic acid sequences to which they are linked.

Such a promoter can be a *Lawsonia* promoter e.g. the promoter involved in in vivo expression of the 19/21 kD, the 37 kD or the 50 kD gene, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771–775, 1982); the bacteriophage lambda promoters and operators (Remaut, E. et al., Nucl. Acids Res., 11, 4677–4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p 10 promoters of baculoviruses can be used (Smith, G. E. et al., Mol. Cell. Biol. 3, 2156–65, 1983). When the host cell is of mammalian origin illustrative useful expression control sequences include the SV-40 promoter (Berman, P. W. et al., Science, 222, 524–527, 1983) or the metallothionein promoter (Brinster, R. L., Nature, 296, 39–42, 1982) or a heat shock promoter (Voellmy et al., Proc. Natl. Acad. Sci. USA, 82, 4949–53, 1985).

Bacterial, yeast, fungal, insect and mammalian cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in U.S. NTIS Publication Ser. No. 08/043,109 (Hoffman, S. and Rogers, W.: Public. Date 1 Dec. 1993).

A still even more preferred form of this embodiment of the invention relates to Live Recombinant Carriers (LRCs) comprising a nucleic acid sequence encoding the 19/21 kD, 37 kD or 50 kD protein or an immunogenic fragment thereof according to the invention, a DNA fragment according to the invention or a recombinant DNA molecule according to the invention. Such carriers are e.g. bacteria and viruses. These LRCs are micro-organisms or viruses in which additional genetic information, in this case a nucleic acid sequence encoding the 19/21 kD, 37 kD or 50 kD protein or an immunogenic fragment thereof according to the invention has been cloned. Animals infected with such LRCs will produce an immunogenic response not only against the immunogens of the carrier, but also against the immunogenic parts of the protein(s) for which the genetic code is additionally cloned into the LRC, e.g. the 19/21 kD, 37 kD or 50 kD gene. As an example of bacterial LRCs, attenuated *Salmonella* strains known in the art can attractively be used.

Live recombinant carrier parasites have i.a. been described by Vermeulen, A. N. (Int. Journ. Parasitol. 28: 1121–1130 (1998)).

Also, LRC viruses may be used as a way of transporting the nucleic acid sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92–99 (1989)).

The technique of in vivo homologous recombination, well-known in the art, can be used to introduce a recombinant nucleic acid sequence into the genome of a bacterium, parasite or virus of choice, capable of inducing expression of the inserted nucleic acid sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier containing a nucleic acid molecule encoding a 19/21 kD, 37 kD or 50 kD protein or a fragment thereof according to the invention.

A host cell may be a cell of bacterial origin, e.g. *Escherichia coli*, *Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47–55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel proteins: the 19/21 kD protein, the 37 kD and 50 kD protein and to immunogenic fragments thereof according to the invention.

The concept of immunogenic fragments will be defined below.

One form of this embodiment relates i.a to *Lawsonia intracellularis* proteins that have an amino acid sequence that is at least 70% homologous to the amino acid sequence as depicted in SEQ ID NO: 2 and to immunogenic fragments of said protein.

In a preferred form, the embodiment relates to such *Lawsonia intracellularis* proteins that have a sequence homology of at least 80%, preferably 90%, more preferably 95% homology to the amino acid sequence as depicted in SEQ ID NO: 2 and to immunogenic fragments of such proteins.

Even more preferred is a homology level of 98% or even 100%.

Another form of this embodiment relates i.a. to *Lawsonia intracellularis* proteins that have an amino acid sequence that is at least 70% homologous to the amino acid sequence as depicted in SEQ ID NO: 4 and to immunogenic fragments of said protein.

A preferred form relates to such *Lawsonia intracellularis* proteins that have a sequence homology of at least 80%, preferably 90%, more preferably 95% homology to the amino acid sequence as depicted in SEQ ID NO: 4 and to immunogenic fragments of such proteins.

Even more preferred is a homology level of 98% or even 100%.

Still another form of this embodiment relates to a *Lawsonia intracellularis* Outer Membrane Protein having a molecular weight of 19/21 kD, which Outer Membrane Protein is obtainable by a process comprising the steps of
a) subjecting an outer membrane preparation to SDS-PAGE
b) excision of the 19 or 21 kD band from the gel
and to immunogenic fragments of that protein.

In Example 1, an example of how to take these steps is explained in detail: first the step of isolation of *L. intracellularis* from infected porcine ilea is described, followed by a description, of how to obtain a *L. intracellularis* outer membrane protein preparation. Finally, under "Outer membrane protein sequencing" it is explained how to isolate the 19 or 21 kD band from the gel.

In a preferred form this *Lawsonia intracellularis* protein or an immunogenic fragment of that protein has an internal amino acid sequence that is at least 70% homologous to the amino acid sequence as depicted in SEQ ID NO: 5, an internal amino acid sequence that is at least 70% homologous to the amino acid sequence as depicted in SEQ ID NO: 6 or an internal amino acid sequence that is at least 70% homologous to the amino acid sequence as depicted in SEQ ID NO: 7.

In a more preferred form, this *Lawsonia intracellularis* protein or an immunogenic fragment of that protein has a sequence homology of at least 80%, preferably 90%, more preferably 95% homology to the amino acid sequence as depicted in SEQ ID NO: 5, 6 or 7. Even more preferred is a homology level of 98% or even 100%.

The level of protein homology can be determined with the computer program "BLAST 2 SEQUENCES" by selecting sub-program: "BLASTP."

A reference for this program is Tatiana A. Tatusova, Thomas L. Madden FEMS Microbiol. Letters 174: 247–250 (1999). Matrix used: "blosum62". Parameters used are the default parameters:

Open gap: 11. Extension gap: 1. Gap x_dropoff: 50.

It will be understood that, for the particular proteins embraced herein, natural variations can exist between individual *Lawsonia intracellularis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435–1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity. This explains why *Lawsonia intracellularis* proteins according to the invention, when isolated from different field isolates, may have homology levels of about 70%, while still representing the same protein with the same immunological characteristics. Those variations in the amino acid sequence of a certain protein according to the invention that still provide a protein capable of inducing an immune response against infection with *Lawsonia intracellularis* or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in the host, i.e. comprises a B- or T-cell epitope. At this moment, a variety of techniques is available to easily identify DNA fragments encoding antigenic fragments (determinants). The method described by Geysen et al (Patent Application WO 84/03564, Patent Application WO 86/06487, U.S. Pat. No. R. 4,833,092, Proc. Natl Acad. Sci. 81: 3998–4002 (1984), J. Imm. Meth. 102, 259–274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248–3828 (1981)), and the secondary structure aspects according to Chou and Fasman (Advances in Enzymology 47: 45–148 (1987) and U.S. Pat. No. 4,554, 101). T-cell epitopes can likewise be predicted from the sequence by computer with the aid of Berzofsky's amphiphilicity criterion (Science 235, 1059–1062 (1987) and U.S. patent application NTIS Ser. No. 07/005,885). A condensed overview is found in: Shan Lu on common principles: Tibtech 9: 238–242 (1991), Good et al on Malaria epitopes; Science 235: 1059–1062 (1987), Lu for a review; Vaccine 10: 3–7 (1992), Berzowsky for HIV-epitopes; The FASEB Journal 5: 2412–2418 (1991).

Therefore, one form of still another embodiment of the invention relates to vaccines capable of protecting pigs against *Lawsonia intracellularis* infection, that comprise one or more proteins or immunogenic fragments thereof, according to the invention as described above together with a pharmaceutically acceptable carrier.

Still another embodiment of the present invention relates to the proteins according to the invention for use in a vaccine.

Still another embodiment relates to the use of a protein according to the invention for the manufacturing of a vaccine for combating *Lawsonia intracellularis* infections.

One way of making a vaccine according to the invention is by biochemical purification of the proteins or immunogenic fragments thereof according to the invention from bacteria obtained through mucosal scrapings taken from the infected intestine wall. This is however a very time-consuming way of making the vaccine.

It is therefore much more convenient to use the expression products of the genes encoding the proteins or immunogenic fragments thereof according to the invention in vaccines. The nucleic acid sequences of the genes encoding the 37 kD and 50 kD proteins are presented in the present invention. The gene encoding the 19/21 kD protein can easily be located and isolated using mixed probe hybridisation as described in Maniatis (Maniatis/Sambrook (Sambrook, J. Molecular cloning: a laboratory manual, 1989. ISBN 0-87969-309-6). The amino acid sequences presented in SEQ ID NO: 5, 6 and 7 form the basis for mixed probes with the following sequences:

| Peptide 1 | Peptide 2 | Peptide 3 |
|---|---|---|
| Forward primers | Forward primers | Forward primer |
| ggI acI caR gaR taY aaY tt SEQ ID NO: 21 ggI acI caR gaR taY aaY ct SEQ ID NO: 22 | gcI taY gaY taY ttR gtI atg SEQ ID NO: 25 gcI taY gaY taY ctI gtI atg SEQ ID NO: 26 | TtY taY gtI atg gtI tgg ac SEQ ID NO: 29 |
| Reverse primers | Reverse primers | Reverse primer |
| AaR ttR taY tcY tgI gtI cc SEQ ID NO: 23 | cat Iac Yaa Rta Rtc Rta Igc SEQ ID NO: 27 | Gtc caI acc atI acR taR aa SEQ ID NO: 30 |

-continued

| Peptide 1 | Peptide 2 | Peptide 3 |
|---|---|---|
| AaR ttR taY tcY tgI gtI cc SEQ ID NO: 24 | cat Iac Iag Rta Rtc Rta Igc SEQ ID NO: 28 | |

With the use of these sequences, the gene encoding the 19/21 kD protein can be located and isolated, equal to the way the genes encoding the 37 kD and 50 kD proteins have been isolated (see Example 1; "Amplification of outer membrane protein genes").

Such vaccines based upon the expression products of these genes can easily be made by admixing one or more proteins according to the invention or immunogenic fragments thereof according to the invention with a pharmaceutically acceptable carrier as described below.

Alternatively, a vaccine according to the invention can comprise live recombinant carriers as described above, capable of expressing the proteins according to the invention or immunogenic fragments thereof according to the invention. Such vaccines, e.g. based upon a *Salmonella* carrier or a viral carrier infecting the gastric epithelium have the advantage over subunit vaccines that they better mimic the natural way of infection of *Lawsonia intracellularis*. Moreover, their self-propagation is an advantage since only low amounts of the recombinant carrier are necessary for immunisation.

Vaccines described above all contribute to active vaccination, i.e. the host's immune system is triggered by one or more proteins according to the invention or immunogenic fragments thereof, to make antibodies against these proteins. Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Lawsonia intracellularis* can in these cases bind directly to the bacteria. This has the advantage that it immediately decreases or stops *Lawsonia intracellularis* growth. Therefore, one other form of this embodiment of the invention relates to vaccines comprising antibodies against any of the three *Lawsonia intracellularis* proteins according to the invention.

Vaccines can also be based upon host cells as described above, that comprise the proteins or immunogenic fragments thereof according to the invention.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20–26 (1993)).

This way of vaccination is very attractive for the vaccination of pigs against *Lawsonia intracellularis* infection.

Therefore, still other forms of this embodiment of the invention relate to vaccines comprising nucleic acid sequences encoding a protein according to the invention or immunogenic fragments thereof according to the invention, and to vaccines comprising DNA fragments that comprise such nucleic acid sequences.

Still other forms of this embodiment relate to vaccines comprising recombinant DNA molecules according to the invention.

DNA vaccines can easily be administered through intradermal application e.g. using a needle-less injector. This way of administration delivers the DNA directly into the cells of the animal to be vaccinated. Amounts of DNA in the microgram range between 1 and 100 µg provide very good results.

In a further embodiment, the vaccine according to the present invention additionally comprises one or more antigens derived from other pig pathogenic organisms and viruses, or genetic information encoding such antigens.

Such organisms and viruses are preferably selected from the group of Pseudorabies virus, Porcine influenza virus, Porcine parvo virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein according to the invention, or an immunogenic fragment thereof, and a pharmaceutically acceptable carrier.

Vaccines according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyldipeptides, Quill A®, mineral oil e.g. Bayol® or Markol®, vegetable oil, and Carbopol® (a homopolymer), or Diluvac® Forte. The vaccine may also comprise a so-called "vehicle". A vehicle is a compound to which the polypeptide adheres, without being covalently bound to it. Often used vehicle compounds are e.g. aluminium hydroxide, -phosphate or -oxide, silica, Kaolin, and Bentonite.

A special form of such a vehicle, in which the antigen is partially embedded in the vehicle, is the so-called ISCOM (EP 109.942, EP 180.564, EP 242.380).

In addition, the vaccine may comprise one or more suitable surface-active compounds or emulsifiers, e.g. Span or Tween.

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvating, adding vehicle compounds or diluents, emulsifying or stabilising a polypeptide are also embodied in the present invention.

Vaccines according to the invention can very suitably be administered in amounts ranging between 1 and 100 micrograms, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Many ways of administration can be applied. Systemic application is a suitable way of administration, e.g. by intramuscular application of the vaccine. If this route is followed, standard procedures known in the art for systemic application are well-suited. Oral application is also an attractive way of administration, because the infection is an infection of the digestive tract. A preferred way of oral administration is the packaging of the vaccine in capsules, known and frequently used in the art, that only disintegrate in the highly acidic environment of the stomach. Also, the vaccine could be mixed with compounds known in the art for temporarily enhancing the pH of the stomach.

Systemic application is also suitable, e.g. by intramuscular application of the vaccine. If this route is followed, standard procedures known in the art for systemic application are well-suited.

From a point of view of protection against disease, a quick and correct diagnosis of *Lawsonia intracellularis* infection is important.

Therefore it is another objective of this invention to provide diagnostic tools suitable for the detection of *Lawsonia intracellularis* infection.

A diagnostic test for the detection of *Lawsonia intracellularis* is e.g. based upon the reaction of bacterial DNA isolated from the animal to be tested, with specific probes or PCR-primers based upon the coding sequence of the 19/21 kD, the 37 kD or the 50 kD genes. If *Lawsonia intracellularis* DNA is present in the animal, this will e.g. specifically bind to specific PCR-primers and will subsequently become amplified in PCR-reaction. The PCR-reaction product can then easily be detected in DNA gel electrophoresis. The DNA can most easily be isolated from the micro-organisms present in swabs taken from the digestive tract of the animal to be tested. Standard PCR-textbooks give methods for determining the length of the primers for selective PCR-reactions with *Lawsonia intracellularis* DNA. Primers with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler; PCR primers, a laboratory manual. ISBN 0-87969-447-5 (1995)).

Nucleic acid sequences encoding a *Lawsonia intracellularis* protein or parts of those nucleic acid sequences having a length of at least 12, preferably 15, more preferably 18, even more preferably 20, 22, 25, 30, 35 or 40 nucleotides in that order of preference, wherein the nucleic acid sequences or parts hereof have at least 70% homology with the nucleic acid sequence as depicted in SEQ ID NO: 1 or 3. Are therefore also part of the invention. Such nucleic acid sequences can be used as primers in PCR-reactions in order to enhance the amount of DNA that they encode. This allows the quick amplification of specific nucleotide sequences for use as a diagnostic tool for e.g. the detection of *Lawsonia* in tissue as indicated above.

Another DNA-based test is based upon growth of bacterial material obtained from the swab, followed by classical DNA purification followed by classical hybridisation with radioactively or colour-labelled 19/21 kD, 37 kD or 50 kD protein-specific DNA-fragments. Both PCR-reactions and hybridisation reactions are well-known in the art and are i.a. described in Maniatis/Sambrook (Sambrook, J. et al. Molecular cloning: a laboratory manual. ISBN 0-87969-309-6).

Thus, one embodiment of the invention relates to a diagnostic test for the detection of *Lawsonia intracellularis* DNA. Such a test comprises a nucleic acid sequence according to the invention or a fragment thereof that is specific for the DNA encoding the 19/21 kD, 37 kD or 50 kD protein. A fragment that is specific for that DNA is understood to be a fragment that, under comparable conditions, binds better to the *Lawsonia intracellularis* DNA than to DNA of other bacteria, due to higher homology with the *Lawsonia intracellularis* DNA, e.g. a primer of at least 12 nucleotides as described above.

A diagnostic test for the detection of *Lawsonia intracellularis* antibodies in sera can be e.g. a simple standard sandwich-ELISA-test in which 19/21 kD, 37 kD or 50 kD protein or antigenic fragments thereof according to the invention are coated to the wall of the wells of an ELISA-plate. A method for the detection of such antibodies is e.g. incubation of 19/21 kD, 37 kD or 50 kD protein or antigenic fragments thereof with serum from mammals to be tested, followed by e.g. incubation with a labelled antibody against the relevant mammalian antibody. A colour reaction can then reveal the presence or absence of antibodies against *Lawsonia intracellularis*. Another example of a diagnostic test system is e.g. the incubation of a Western blot comprising the 19/21 kD, 37 kD or 50 kD protein or an antigenic fragment thereof according to the invention, with serum of mammals to be tested, followed by analysis of the blot.

Thus, another embodiment of the present invention relates to diagnostic tests for the detection of antibodies against *Lawsonia intracellularis*. Such tests comprise a protein or a fragment thereof according to the invention.

Also, the invention relates to methods for the detection in serum of antibodies against *Lawsonia intracellularis*, in which the method comprises the incubation of serum with the 19/21 kD, 37 kD or 50 kD protein or antigenic fragments thereof according to the invention.

A diagnostic test based upon the detection of antigenic material of the specific 19/21 kD, 37 kD and 50 kD proteins of *Lawsonia intracellularis* antigens and therefore suitable for the detection of *Lawsonia intracellularis* infection can e.g. also be a standard ELISA test. In one example of such a test the walls of the wells of an ELISA plate are coated with antibodies directed against the 19/21 kD, 37 kD or 50 kD protein. After incubation with the material to be tested, labelled anti-*Lawsonia intracellularis* antibodies are added to the wells. A colour reaction then reveals the presence of antigenic material from *Lawsonia intracellularis*.

Therefore, still another embodiment of the present invention relates to diagnostic tests for the detection of antigenic material of *Lawsonia intracellularis*. Such tests comprise antibodies against a protein or a fragment thereof according to the invention.

The polypeptides or immunogenic fragments thereof according to the invention expressed as characterised above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the polypeptide according to the invention (or variants or fragments thereof) according to the present invention, can be prepared by immunising inbred mice by techniques also known in the art (Kohler and Milstein, *Nature*, 256, 495–497, 1975).

Still another embodiment of the invention relates to methods for the detection of antigenic material from *Lawsonia intracellularis* in which the method comprises the incubation of serum, tissue of body fluids with antibodies against the 19/21 kD, the 37 kD or the 50 kD protein or an antigenic fragment thereof according to the invention.

Finally, an embodiment of the invention relates to nucleic acid sequences encoding a *Lawsonia intracellularis* protein or parts of those nucleic acid sequences having a length of at least 20, preferably 25, 30, 35 or 40 nucleotides in that order of preference, wherein the nucleic acid sequences or parts hereof have at least 70% homology with the nucleic acid sequence as depicted in SEQ ID NO: 1 or 3. Such nucleic acid sequences can be used as primers in PCR-reactions in order to enhance the amount of DNA that they encode. This allows the quick amplification of specific nucleotide sequences for use as a diagnostic tool for e.g. the detection of *Lawsonia* in tissue as indicated above.

EXAMPLES

Example 1

Isolation of *L. intracellularis* from Infected Porcine Ilea.

*L. intracellularis* infected ilea, confirmed by histopathology and acid-fast Ziehl-Neelsen staining, were collected from pigs died with PE, and stored at −80° C. After thawing *L. intracellularis* bacteria were isolated from mucosal scrapings taken from the infected intestinal wall. The ilea, scrapings were homogenized repeatedly in PBS in an omnimixer to release the intracellular bacteria as described by Lawson et al. (Vet. Microbiol. 10: 303–323 (1985)). Supernatant obtained after low-speed centrifugation to remove cell debris was filtered through 5.0, 3.0, 1.2, and 0.8 μm filters (Millipore). The filtrate was subsequently centrifuged at 8000 g for 30 min, giving a small pallet of *L. intracellularis* bacteria. These bacteria were further purified using a Percoll gradient. The identity of the purified bacteria was assessed by PCR (Jones et al., J. Clin. Microbiol. 31: 2611–2615 (1993)) whereas purity of the isolated bacteria (>95%) was assessed by phase contrast microscopy to reveal any contaminating bacteria or gut debris present.

*L. intracellularis* Outer Membrane Protein Preparation

Outer membrane proteins (OMP) from *L. intracellularis* were purified essentially as described by Barenkamp et al., J. Inf. Dis. 148: 1127 ($_{1983}$)). Briefly, Percoll-gradient-purified bacteria were disrupted ultrasonically. Membrane fragments were harvested by differential centrifugation, treated with Sarkosyl and insoluble Sarkosyl OMPs were pelleted by ultracentrifugation. The pellet was redissolved in 50 mM TRIS/HCl (pH 7.5). The OMP's were separated on a 4–12% BIS/TRIS NuPAGE SDS polyacrylamide gel (NOVEX) according the description of the manufacturer (FIG. 1; panel A). In the adjacent lane total *L. intracellularis* cell protein was loaded for comparison reasons.

The proteins were stained using Coomassie Brilliant Blue R250. In the outer membrane preparation clearly visible enhancement of protein bands at 50, 37, and 19/21 kDa could be seen in comparison to whole cell preparation, indicating that these proteins are OMPs.

Antisera Raised Against Purified Outer Membrane Proteins and Whole Cells, and after Experimental Challenge Antisera to *L. intracellularis* whole cells and purified OMPs were raised in rabbits. Rabbits were injected intramuscularly with a preparation of whole cell (R291) or OMPs (R279) in n-GNE (water:oil=45:55). Blood samples were collected from the ear vein prior to immunization. Serum was also obtained from a pig that had been experimentally challenged orally with Percoll-gradient-purified bacteria and had developed clinical signs and post-mortem lesions typical for *L. intracellularis* infection (BIG304T4).

Antigenic Characterization of *L. intracellularis* Outer Membrane Proteins

To investigate the antigenicity of the *L. intracellularis* OMPs, the OMP preparation was loaded on a 4–12% BIS/TRIS NuPAGE SDS-PAGE (NOVEX). After separation the proteins we blotted to Immobilon-P PVDF membrane (Millipore) in 0.025 M TRIS/0.192 M glycine/20% methanol basically according to Towbin et al. (Natl. Proc. Acad. Sci., 76: 4350–4354 (1979)). Membranes were blocked with 1% skimmed milk powder in 0.04 M PBS containing 0.05% Tween 20 (PBST) and then incubated with rabbit R279 antiserum (FIG. 1; panel B) and rabbit R291 antiserum (FIG. 1; panel C) for 1 hour followed by washing twice with PBST. Rabbit sera were used at a dilution of 500 in 1% skimmed milk/PBST. HRP-conjugated goat anti-rabbit immunoglobulins, diluted 1:2000, were applied to detect the rabbit antibodies. Seroreactive products were detected by Enhanced Chemoluminescence (ECL, Amersham) according the manufacturers protocol.

Both antisera (R279 and R291) recognized the proteins described above. Signals at 50 and 37 kDa increased mostly comparing whole cell protein with OMPs preparation again indicating that these two proteins are OMPs.

Outer Membrane Protein Sequencing

For sequencing purposes the OMP suspension was loaded on a preparative 10% SDS-PAGE gel using the BioRad Protean II system according to the manual. Four protein bands (19/21, 37 and 50 kD) were cut out of the gel and were shipped to Eurosequence (Groningen, The Netherlands) at 4° C. The protein sequences of N-terminus and of isolated peptides obtained after tryptic digest of the whole protein were determined by automated Edman degradation on a Applied Biosystems 120A PTH Sequenator. The obtained protein sequences (Table 1) were used for the generation of PCR primers for the amplification of the encoding genes. From the protein sequences it was concluded that the 19 kD and 21 kD protein basically represent the same protein. The difference in size is probably due a post-translational modification(s).

Amplification of Outer Membrane Protein Genes

In order to amplify OMP genes, *L. intracellularis* genomic DNA was isolated from Percoll-gradient-purified bacteria using QIAGEN Genomic Tip 100 as described by the manufacturer. This DNA was used in PCR using degenerated primers based on obtained protein sequences. The DNA encoding the 50 ID protein was amplified using primers 911 (ggI gtI tgg gaY ttY aa) and 912 (tcc caI gcR taR tcY tt). The DNA encoding the 37 kD protein was amplified using primers 990 (tcR aaI gcR aaR ttIacI cc) and 1021 (gcI gaR gtI acI gcI ag) using the EXPAND system (Boehringer Mannheim) with 2.5 mM MgCl$_2$. Then, 1 µl from the PCR mixture was taken and used in a nested PCR using the same primers. This gave bands of 1260 bp and 656 bp for the 50 kD and 37 kD protein respectively. PCR products were cut out from agarose gel and purified using QIAGEN spinprep kit and cloned into pCR-TOPO-blunt II (Novagen). The cloning mix was transformed to *E. coli* TOP10F. Putative transformants were screened for inserts by colony PCR, using M13 forward and M13 reverse primers. From the putative clones containing a plasmid with insert, plasmid DNA was isolated using QIAGEN miniprep Kit. Subsequently, inserts were sequenced using the PRISM Ready Reaction DyeDeoxy Terminator Sequencing Kit (Applied Biosystems) according manufacturers protocol using the M13 forward and reverse primers.

The C-terminal part of the 50 kD coding region was amplified using c-tailing PCR using primer 923 (tat agc tgt tga tgg tgc tt) in the first PCR and 936 (ggt gat aat atg ctt tac t) and a poly-G primer (ata tgg ggg ggg ggg ggg g) in the nested PCR. This gave a band of 840 bp, which was cloned and sequenced as above.

Cloning of the DNA Encoding the 50 kD Protein in pET24a

With *L. intracellularis* chromosomal DNA as template the DNA coding for the mature part of the 50 kD protein was amplified using primers 967 (gga att cca tat gta ttg att tta agg caa a) and 968 (cgc gga tcc gcg atc ctt gat aat tca agg) and the EXPAND system. The PCR product was isolated from gel and cut with NdeI and BamHI and ligated into NdeI and BamHI cut pET24a (Novagen) giving plasmid pP5-a. Theoretically, induction of pP5-a mediated 50 kD protein expression should yield a 50 kD protein localized in the cytoplasm, because protein sequence analysis of cloned P5 did not lead to the identification of an excretion signal of any kind. It has been well established that OMPs only fold properly and therefor are only antigenically active, when expression is followed by export to its natural localization, the outer membrane. To allow export of the 50 kD protein to the outer membrane overlap extension PCR was applied using primers 972 (gga att cca tat gaa aat gaa aaa gag cac tct ggc) and 969 (ccg ctc gag gaa ttg ata ctt cat att taa) to fuse the *E. coli* phoE signal sequence in front of the mature 50 kD protein. The construct was cloned in pCR-TOPO-blunt II. After identification of the right clone by sequencing the insert was excised from pCR-TOPO-blunt II plasmid using NdeI and XhoI. The DNA fragment was then ligated into NdeI and XhoI cut pET24a giving plasmid pP5-f. Primer 969 was designed in such that cloning led to the addition of 6×His-tag at the C-terminal portion of the 50 kD protein.

Overexpression of the 50 kD Protein in *E. coli* BL21(DE3)

Figure 2:
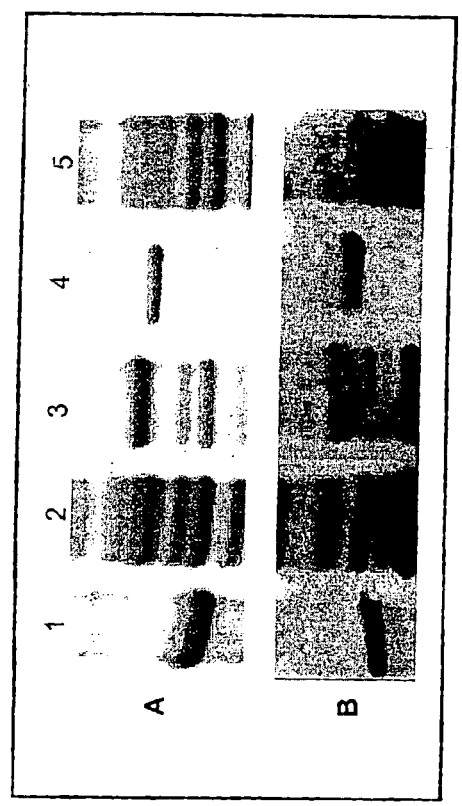
FIG. 2. Overexpression of the 50 kD protein. The protein was overexpressed in BL21(DE3) containing various pET24a-derived constructs as described in text. Total cell extracts were separated by SDS-PAGE and either stained with Coomassie brilliant blue (Panel A) or blotted on an Immobilon-P PVDF membrane and probed with antiserum obtained from experimentally infected pigs (Panel B). Lane 1: pre-stained precision marker (BioRad) band of 45 kDa; lane 2: BL21-P5-a; Lane 3: BL21-P5-f; lane 4: purified *L. intracellularis* outer membrane proteins (only 50 kD protein visible). Lane 5: BL21-P5-a uninduced.

Plasmids pP5-a and pP5-f were transformed to BL21 (DE3). The obtained strains BL21-P5-a and BL21-P5-f were after o/n growth a rotary shaker (180 rpm) at 37° C., 1:100 diluted in fresh 5 ml LB. After 3 hours growth the T7 RNA polymerase was induced with 50 µM isopropylthiogalactoside (IPTG), and cultivation was continued for 3 hours. Cells were harvested by centrifugation and samples were loaded with the appropriate controls on two 4–12% BIS/TRIS NuPAGE SDS polyacrylamide gel (NOVEX) according the description of the manufacturer. The first gel was stained with Coomassie brilliant blue 250R (FIG. 2; panel A). The second gel was used for Western blotting. The blot was probed with pig serum (BIG304T4; FIG. 2; panel B).

After induction an extra protein band appeared in strain BL21-P5-a (lane 2) and BL21-P5-f (lane 3) which is lacking in the negative control (lane 5). The protein produced in strain BL21-P5-f ran at a slightly higher molecular weight as the native 50 kD protein (lane 4) probably due to the C-terminal His-tag.

TABLE 1

Obtained protein sequences

| Protein | Peptide | Sequence | Sequence Id No: |
|---|---|---|---|
| 19 kD | Internal | AAYEYLVMLGVN | SEQ ID NO: 5 |
| | Internal | PFYVMVW | SEQ ID NO: 31 |
| | Internal | GTQEYNLALGER | SEQ ID NO: 6 |
| 21 kD | Internal | AAYEYLVMLGVN | SEQ ID NO: 5 |
| | Internal | PFYVMVW | SEQ ID NO: 7 |
| | Internal | GTQEYNLALGER | SEQ ID NO: 6 |
| 37 kD | N-terminal | AEVTASCTKRVG | SEQ ID NO: 15 |
| | Internal | SDLEIFGR | SEQ ID NO: 32 |
| | Internal | GVNFAFDSFALDDTAK | SEQ ID NO: 16 |
| 50 kD | N-terminal | IDFKAKGVWDFN | SEQ ID NO: 17 |
| | Internal | KDYAWBVDFDT | SEQ ID NO: 18 |

We claim:

1. An isolated and purified *Lawsonia intracellularis* outer membrane protein, comprising the amino acid sequence as set forth in SEQ ID NO: 2 and having a molecular weight of about 37 kD as determined by sodium dodecyl sulphate polyacrylamide gel electrophoresis.

2. An immunogenic composition comprising an immunogenically effective amount of the protein according to claim 1, and a pharmaceutically acceptable carrier.

3. An immunogenic composition according to claim 2, further comprising an adjuvant.

4. The immunogenic composition according to claim 2, further comprising at least one antigen in addition to the *Lawsonia intracellularis* outer membrane protein obtained from a virus or micro-organism pathogenic to pigs.

5. The immunogenic composition according to claim 4, wherein said virus or micro-organism pathogenic to pigs is selected from the group consisting of Pseudorabies virus, Porcine influenza virus, Porcine parvo virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

* * * * *

SEQUENCE LISTING

<160> NUMBER OF SEQ ID NOS: 32

<210> SEQ ID NO 1
<211> LENGTH: 656
<212> TYPE: DNA
<213> ORGANISM: Lawsonia intracellularis
<220> FEATURE:
<221> NAME/KEY: CDS
<222> LOCATION: (1)..(654)

<400> SEQUENCE: 1

```
gcg gag gtg acg gcg agt tgt act aaa cgt gtt gaa agc tat aat tat       48
Ala Glu Val Thr Ala Ser Cys Thr Lys Arg Val Glu Ser Tyr Asn Tyr
 1               5                  10                  15 ctt gtg gat tat tca ggc tct atg atg atg aaa cat gtt gct gtt aga       96
Leu Val Asp Tyr Ser Gly Ser Met Met Met Lys His Val Ala Val Arg
             20                  25                  30 gag cct aaa ata gaa tta gca aaa gaa gct ata tta aaa att aat gcg      144
Glu Pro Lys Ile Glu Leu Ala Lys Glu Ala Ile Leu Lys Ile Asn Ala
         35                  40                  45 gca atg cct aaa atg tca tat caa ggt gga tta tat act ttt gca cct      192
Ala Met Pro Lys Met Ser Tyr Gln Gly Gly Leu Tyr Thr Phe Ala Pro
 50                  55                  60 tat tct gta att att ccc caa ggt tct tgg aat tca tgt gtt gcc gaa      240
Tyr Ser Val Ile Ile Pro Gln Gly Ser Trp Asn Ser Cys Val Ala Glu
 65                  70                  75                  80 tgt gcg gtt aat aca att aag tct gat tta gaa att ttt ggt cgt ctt      288
Cys Ala Val Asn Thr Ile Lys Ser Asp Leu Glu Ile Phe Gly Arg Leu
                 85                  90                  95 act cct gtg gga gac ggc ata aaa atg cat gaa aca gtc att aat caa      336
Thr Pro Val Gly Asp Gly Ile Lys Met His Glu Thr Val Ile Asn Gln
            100                 105                 110 atg ccc cct cag gca gcc gtt att ctt ctc act gat ggt cat aat aat      384
Met Pro Pro Gln Ala Ala Val Ile Leu Leu Thr Asp Gly His Asn Asn
        115                 120                 125 tta ggg atg aat cct gtt gag gaa gta aaa tct ata tat caa aca aat      432
Leu Gly Met Asn Pro Val Glu Glu Val Lys Ser Ile Tyr Gln Thr Asn
    130                 135                 140 cct aat gtt tgt ttt cat gta gtt tca ttt gca gat gat gct gaa ggc      480
Pro Asn Val Cys Phe His Val Val Ser Phe Ala Asp Asp Ala Glu Gly
145                 150                 155                 160 aaa gca ata att gat caa att gtt gca ctt aat agt gga agt gtt ctt      528
Lys Ala Ile Ile Asp Gln Ile Val Ala Leu Asn Ser Gly Ser Val Leu
                165                 170                 175 gtt gat ggt tta cag ctt cta caa aat cct gct gtt tgc caa gaa ttt      576
Val Asp Gly Leu Gln Leu Leu Gln Asn Pro Ala Val Cys Gln Glu Phe
            180                 185                 190 gtt aat agt gtt ttt tgt caa gag caa att ctt gtt aca gaa gaa gtt      624
Val Asn Ser Val Phe Cys Gln Glu Gln Ile Leu Val Thr Glu Glu Val
        195                 200                 205 gtt gta ctt cgt ggc gtc aac ttt gcc ttc ga                           656
Val Val Leu Arg Gly Val Asn Phe Ala Phe
    210                 215
```

<210> SEQ ID NO 2
<211> LENGTH: 218
<212> TYPE: PRT
<213> ORGANISM: Lawsonia intracellularis -continued

```
<400> SEQUENCE: 2

Ala Glu Val Thr Ala Ser Cys Thr Lys Arg Val Glu Ser Tyr Asn Tyr
  1               5                  10                  15

Leu Val Asp Tyr Ser Gly Ser Met Met Met Lys His Val Ala Val Arg
             20                  25                  30

Glu Pro Lys Ile Glu Leu Ala Lys Glu Ala Ile Leu Lys Ile Asn Ala
         35                  40                  45

Ala Met Pro Lys Met Ser Tyr Gln Gly Gly Leu Tyr Thr Phe Ala Pro
     50                  55                  60

Tyr Ser Val Ile Ile Pro Gln Gly Ser Trp Asn Ser Cys Val Ala Glu
 65                  70                  75                  80

Cys Ala Val Asn Thr Ile Lys Ser Asp Leu Glu Ile Phe Gly Arg Leu
                 85                  90                  95

Thr Pro Val Gly Asp Gly Ile Lys Met His Glu Thr Val Ile Asn Gln
            100                 105                 110

Met Pro Pro Gln Ala Ala Val Ile Leu Leu Thr Asp Gly His Asn Asn
        115                 120                 125

Leu Gly Met Asn Pro Val Glu Glu Val Lys Ser Ile Tyr Gln Thr Asn
    130                 135                 140

Pro Asn Val Cys Phe His Val Val Ser Phe Ala Asp Asp Ala Glu Gly
145                 150                 155                 160

Lys Ala Ile Ile Asp Gln Ile Val Ala Leu Asn Ser Gly Ser Val Leu
                165                 170                 175

Val Asp Gly Leu Gln Leu Leu Gln Asn Pro Ala Val Cys Gln Glu Phe
            180                 185                 190

Val Asn Ser Val Phe Cys Gln Glu Gln Ile Leu Val Thr Glu Glu Val
        195                 200                 205

Val Val Leu Arg Gly Val Asn Phe Ala Phe
    210                 215

<210> SEQ ID NO 3
<211> LENGTH: 1428
<212> TYPE: DNA
<213> ORGANISM: Lawsonia intracellularis
<220> FEATURE:
<221> NAME/KEY: CDS
<222> LOCATION: (1)..(1425)

<400> SEQUENCE: 3 gct att

-continued

```
cgt atg ggt tta caa cct tat gtc ctt cca gga ttt gtt gca ggt tct      336
Arg Met Gly Leu Gln Pro Tyr Val Leu Pro Gly Phe Val Ala Gly Ser
        100                 105                 110 aca ata tta gat gct gat gga gca ggt gtt act gtt tct gct gta ttt      384
Thr Ile Leu Asp Ala Asp Gly Ala Gly Val Thr Val Ser Ala Val Phe
    115                 120                 125 aat gat tat tta ggt gct aca gct ttc tgg atg cgt gca ttg cat aaa      432
Asn Asp Tyr Leu Gly Ala Thr Ala Phe Trp Met Arg Ala Leu His Lys
130                 135                 140 aac tat gat agt aat tat gga ata tca aag cta cct aac ttt aaa ggt      480
Asn Tyr Asp Ser Asn Tyr Gly Ile Ser Lys Leu Pro Asn Phe Lys Gly
145                 150                 155                 160 aca aca tta gat gta gtt gga tta act att cct gta aca ata tct gat      528
Thr Thr Leu Asp Val Val Gly Leu Thr Ile Pro Val Thr Ile Ser Asp
                165                 170                 175 ata aaa att gct cca tgg ggt atg ttt gct ttt gca ggt aag aag agc      576
Ile Lys Ile Ala Pro Trp Gly Met Phe Ala Phe Ala Gly Lys Lys Ser
            180                 185                 190 tta tta ggg gaa agc tat gga gat att gaa gat gta aga gca ggt ctt      624
Leu Leu Gly Glu Ser Tyr Gly Asp Ile Glu Asp Val Arg Ala Gly Leu
        195                 200                 205 tta cca gca atg cca gca gga ttt gga tat agc tgg gga gct ggt aat      672
Leu Pro Ala Met Pro Ala Gly Phe Gly Tyr Ser Trp Gly Ala Gly Asn
    210                 215                 220 cca ttt gga gat gtt ttt cca aat aaa aag cgt ggt aat gca tgg tgg      720
Pro Phe Gly Asp Val Phe Pro Asn Lys Lys Arg Gly Asn Ala Trp Trp
225                 230                 235                 240 gtt ggt tta tca gct gaa ctt gct ggc tca agt cct ttg cat ata gct      768
Val Gly Leu Ser Ala Glu Leu Ala Gly Ser Ser Pro Leu His Ile Ala
                245                 250                 255 gtt gat ggt gct tat gga cga gca gac tta gga agt ctt aga aat gtt      816
Val Asp Gly Ala Tyr Gly Arg Ala Asp Leu Gly Ser Leu Arg Asn Val
            260                 265                 270 gtt att ggt gac ttc tta cta gat aag att gat tta aaa cgt caa ggt      864
Val Ile Gly Asp Phe Leu Leu Asp Lys Ile Asp Leu Lys Arg Gln Gly
        275                 280                 285 tgg tat gca gca tta tta gca gaa tat aaa ttt gaa tat gta act cca      912
Trp Tyr Ala Ala Leu Leu Ala Glu Tyr Lys Phe Glu Tyr Val Thr Pro
    290                 295                 300 ggg gtt ata ggt tgg tat gcc tca gga gat aaa gtt gat tca cgt ggc      960
Gly Val Ile Gly Trp Tyr Ala Ser Gly Asp Lys Val Asp Ser Arg Gly
305                 310                 315                 320 gcc tct aaa aga ata cca aca tta gtt gga aac tgg tca gca aca agt     1008
Ala Ser Lys Arg Ile Pro Thr Leu Val Gly Asn Trp Ser Ala Thr Ser
                325                 330                 335 ttt gga tat agt gga gcc tat ggt ata ggc aaa gat tct gtt ttt gga     1056
Phe Gly Tyr Ser Gly Ala Tyr Gly Ile Gly Lys Asp Ser Val Phe Gly
            340                 345                 350 aat act att gct ggc tca tgg ggt gtt gta gtt cag ttg aaa gat att     1104
Asn Thr Ile Ala Gly Ser Trp Gly Val Val Gln Leu Lys Asp Ile
        355                 360                 365 tct ttc tta gaa aat cta act cat gtt atc cgt gga gct aga att cag     1152
Ser Phe Leu Glu Asn Leu Thr His Val Ile Arg Gly Ala Arg Ile Gln
    370                 375                 380 ggt aca aat aat aaa gac gtt cct gaa cac tta ggt tta tca tac gtt     1200
Gly Thr Asn Asn Lys Asp Val Pro Glu His Leu Gly Leu Ser Tyr Val
385                 390                 395                 400 act acc att tat gac aca cgt ggt ggt gat aat atg ctt tac tta aca     1248
Thr Thr Ile Tyr Asp Thr Arg Gly Gly Asp Asn Met Leu Tyr Leu Thr
                405                 410                 415
```

-continued

```
aag aaa gat tat gct tgg gaa gta gat ttt gat act gaa tat aaa atc      1296
Lys Lys Asp Tyr Ala Trp Glu Val Asp Phe Asp Thr Glu Tyr Lys Ile
        420                 425                 430 tat aaa gac tta agt gta gct ctt gaa ctg tca tat att cgt ctt gaa      1344
Tyr Lys Asp Leu Ser Val Ala Leu Glu Leu Ser Tyr Ile Arg Leu Glu
        435                 440                 445 ctt gat aaa aaa cta tgg aac ctt caa aga gaa gtt gat aag aat gcc      1392
Leu Asp Lys Lys Leu Trp Asn Leu Gln Arg Glu Val Asp Lys Asn Ala
    450                 455                 460 tat cgt gct ggt tta aat atg aag tat caa ttc taa                      1428
Tyr Arg Ala Gly Leu Asn Met Lys Tyr Gln Phe
465                 470                 475

<210> SEQ ID NO 4
<211> LENGTH: 475
<212> TYPE: PRT
<213> ORGANISM: Lawsonia intracellularis

<400> SEQUENCE: 4

Ala Ile Asp Phe Lys Ala Lys Gly Val Trp Asp Phe Asn Phe Glu Trp
1               5                   10                  15

Gln Gln Ser Ser Phe Met Lys Gly Asp Gly Asp Gln Arg Phe Ser Pro
            20                  25                  30

Lys Gln Arg Leu Arg Thr Gln Ile Asp Ile Val Ala Ser Glu Ser Leu
        35                  40                  45

Lys Gly Val Val Phe Glu Leu Gly Lys Thr Ile Trp Gly Arg Gly
    50                  55                  60

Val Asp Gly Ala Ser Ile Gly Thr Asp Gly Lys Asn Val Ile Lys Leu
65                  70                  75                  80

Arg Tyr Ser Tyr Val Asp Trp Val Ile Pro Tyr Thr Asp Val Gln Val
                85                  90                  95

Arg Met Gly Leu Gln Pro Tyr Val Leu Pro Gly Phe Val Ala Gly Ser
            100                 105                 110

Thr Ile Leu Asp Ala Asp Gly Ala Gly Val Thr Val Ser Ala Val Phe
        115                 120                 125

Asn Asp Tyr Leu Gly Ala Thr Ala Phe Trp Met Arg Ala Leu His Lys
    130                 135                 140

Asn Tyr Asp Ser Asn Tyr Gly Ile Ser Lys Leu Pro Asn Phe Lys Gly
145                 150                 155                 160

Thr Thr Leu Asp Val Val Gly Leu Thr Ile Pro Val Thr Ile Ser Asp
                165                 170                 175

Ile Lys Ile Ala Pro Trp Gly Met Phe Ala Phe Ala Gly Lys Lys Ser
            180                 185                 190

Leu Leu Gly Glu Ser Tyr Gly Asp Ile Glu Asp Val Arg Ala Gly Leu
        195                 200                 205

Leu Pro Ala Met Pro Ala Gly Phe Gly Tyr Ser Trp Gly Ala Gly Asn
    210                 215                 220

Pro Phe Gly Asp Val Phe Pro Asn Lys Lys Arg Gly Asn Ala Trp Trp
225                 230                 235                 240

Val Gly Leu Ser Ala Glu Leu Ala Gly Ser Ser Pro Leu His Ile Ala
                245                 250                 255

Val Asp Gly Ala Tyr Gly Arg Ala Asp Leu Gly Ser Leu Arg Asn Val
            260                 265                 270

Val Ile Gly Asp Phe Leu Leu Asp Lys Ile Asp Leu Lys Arg Gln Gly
        275                 280                 285
```

```
Trp Tyr Ala Ala Leu Ala Glu Tyr Lys Phe Glu Tyr Val Thr Pro
290                 295                 300
Gly Val Ile Gly Trp Tyr Ala Ser Gly Asp Lys Val Asp Ser Arg Gly
305                 310                 315                 320
Ala Ser Lys Arg Ile Pro Thr Leu Val Gly Asn Trp Ser Ala Thr Ser
                325                 330                 335
Phe Gly Tyr Ser Gly Ala Tyr Gly Ile Gly Lys Asp Ser Val Phe Gly
            340                 345                 350
Asn Thr Ile Ala Gly Ser Trp Gly Val Val Gln Leu Lys Asp Ile
                355                 360                 365
Ser Phe Leu Glu Asn Leu Thr His Val Ile Arg Gly Ala Arg Ile Gln
370                 375                 380
Gly Thr Asn Asn Lys Asp Val Pro Glu His Leu Gly Leu Ser Tyr Val
385                 390                 395                 400
Thr Thr Ile Tyr Asp Thr Arg Gly Gly Asp Asn Met Leu Tyr Leu Thr
                405                 410                 415
Lys Lys Asp Tyr Ala Trp Glu Val Asp Phe Asp Thr Glu Tyr Lys Ile
                420                 425                 430
Tyr Lys Asp Leu Ser Val Ala Leu Glu Leu Ser Tyr Ile Arg Leu Glu
            435                 440                 445
Leu Asp Lys Lys Leu Trp Asn Leu Gln Arg Glu Val Asp Lys Asn Ala
450                 455                 460
Tyr Arg Ala Gly Leu Asn Met Lys Tyr Gln Phe
465                 470                 475

<210> SEQ ID NO 5
<211> LENGTH: 12
<212> TYPE: PRT
<213> ORGANISM: Lawsonia intracellularis

<400> SEQUENCE: 5

Ala Ala Tyr Glu Tyr Leu Val Met Leu Gly Val Asn
1               5                   10

<210> SEQ ID NO 6
<211> LENGTH: 12
<212> TYPE: PRT
<213> ORGANISM: Lawsonia intracellularis

<400> SEQUENCE: 6

Gly Thr Gln Glu Tyr Asn Leu Ala Leu Gly Glu Arg
1               5                   10

<210> SEQ ID NO 7
<211> LENGTH: 11
<212> TYPE: PRT
<213> ORGANISM: Lawsonia intracellularis

<400> SEQUENCE: 7

Pro Phe Tyr Val Met Val Trp Thr Pro Arg Arg
1               5                   10

<210> SEQ ID NO 8
<211> LENGTH: 20
<212> TYPE: DNA
<213> ORGANISM: Lawsonia intracellularis

<400> SEQUENCE: 8
tatagctgtt gatggtgctt                                              20
```

<210> SEQ ID NO 9
<211> LENGTH: 19
<212> TYPE: DNA
<213> ORGANISM: Lawsonia intracellularis

<400> SEQUENCE: 9
ggtgataata tgctttact                                                    19

<210> SEQ ID NO 10
<211> LENGTH: 19
<212> TYPE: DNA
<213> ORGANISM: Lawsonia intracellularis

<400> SEQUENCE: 10
atatgggggg ggggggggg                                                    19

<210> SEQ ID NO 11
<211> LENGTH: 31
<212> TYPE: DNA
<213> ORGANISM: Lawsonia intracellularis

<400> SEQUENCE: 11
ggaattccat atgtattgat tttaaggcaa a                                      31

<210> SEQ ID NO 12
<211> LENGTH: 30
<212> TYPE: DNA
<213> ORGANISM: Lawsonia intracellularis

<400> SEQUENCE: 12
cgcggatccg cgatccttga taattcaagg                                        30

<210> SEQ ID NO 13
<211> LENGTH: 36
<212> TYPE: DNA
<213> ORGANISM: Lawsonia intracellularis

<400> SEQUENCE: 13
ggaattccat atgaaaatga aaagagcac tctggc                                  36

<210> SEQ ID NO 14
<211> LENGTH: 30
<212> TYPE: DNA
<213> ORGANISM: Lawsonia intracellularis

<400> SEQUENCE: 14
ccgctcgagg aattgatact tcatatttaa                                        30

<210> SEQ ID NO 15
<211> LENGTH: 12
<212> TYPE: PRT
<213> ORGANISM: Lawsonia intracellularis

<400> SEQUENCE: 15

Ala Glu Val Thr Ala Ser Cys Thr Lys Arg Val Gly
1               5                   10

<210> SEQ ID NO 16
<211> LENGTH: 16
<212> TYPE: PRT
<213> ORGANISM: Lawsonia intracellularis

```
<400> SEQUENCE: 16

Gly Val Asn Phe Ala Phe Asp Ser Phe Ala Leu Asp Asp Thr Ala Lys
1               5                   10                  15

<210> SEQ ID NO 17
<211> LENGTH: 12
<212> TYPE: PRT
<213> ORGANISM: Lawsonia intracellularis

<400> SEQUENCE: 17

Ile Asp Phe Lys Ala Lys Gly Val Trp Asp Phe Asn
1               5                   10

<210> SEQ ID NO 18
<211> LENGTH: 11
<212> TYPE: PRT
<213> ORGANISM: Lawsonia intracellularis

<400> SEQUENCE: 18

Lys Asp Tyr Ala Trp Glu Val Asp Phe Asp Thr
1               5                   10

<210> SEQ ID NO 19
<211> LENGTH: 12
<212> TYPE: PRT
<213> ORGANISM: Lawsonia intracellularis

<400> SEQUENCE: 19

Ala Ala Tyr Glu Tyr Leu Val Met Leu Gly Val Asn
1               5                   10

<210> SEQ ID NO 20
<211> LENGTH: 12
<212> TYPE: PRT
<213> ORGANISM: Lawsonia intracellularis

<400> SEQUENCE: 20

Gly Thr Gln Glu Tyr Asn Leu Ala Leu Gly Glu Arg
1               5                   10

<210> SEQ ID NO 21
<211> LENGTH: 20
<212> TYPE: DNA
<213> ORGANISM: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 21
ggnacncarg artayaaytt                                         20

<210> SEQ ID NO 22
<211> LENGTH: 20
<212> TYPE: DNA
<213> ORGANISM: Primer
<220> FEATURE:
<221> NAME/KEY: misc_feature
<222> LOCATION: (3)..(3)
<223> OTHER INFORMATION: n is a, c, g, or t
```

```
<220> FEATURE:
<221> NAME/KEY: misc_feature
<222> LOCATION: (6)..(6)
<223> OTHER INFORMATION: n is a, c, g, or t

<400> SEQUENCE: 22
ggnacncarg artayaayct                                                    20

<210> SEQ ID NO 23
<211> LENGTH: 20
<212> TYPE: DNA
<213> ORGANISM: Primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 23
aarttrtayt cytgngtncc                                                    20

<210> SEQ ID NO 24
<211> LENGTH: 20
<212> TYPE: DNA
<213> ORGANISM: Primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 24
aarttrtayt cytgngtncc                                                    20

<210> SEQ ID NO 25
<211> LENGTH: 21
<212> TYPE: DNA
<213> ORGANISM: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 25
gcntaygayt ayttrgtnat g                                                  21

<210> SEQ ID NO 26
<211> LENGTH: 21
<212> TYPE: DNA
<213> ORGANISM: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
```

<220> FEATURE:
<221> NAME/KEY: misc_feature
<222> LOCATION: (18)..(18)
<223> OTHER INFORMATION: n is a, c, g, or t

<400> SEQUENCE: 26
gcntaygayt ayctngtnat g                                              21

<210> SEQ ID NO 27
<211> LENGTH: 21
<212> TYPE: DNA
<213> ORGANISM: Primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 27
catnacyaar tartcrtang c                                              21

<210> SEQ ID NO 28
<211> LENGTH: 21
<212> TYPE: DNA
<213> ORGANISM: Primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 28
catnacnagr tartcrtang c                                              21

<210> SEQ ID NO 29
<211> LENGTH: 20
<212> TYPE: DNA
<213> ORGANISM: Primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 29
ttytaygtna tggtntggac                                                20

<210> SEQ ID NO 30
<211> LENGTH: 20
<212> TYPE: DNA
<213> ORGANISM: Primer
<220> FEATURE:
<221> NAME/KEY: misc_feature
<222> LOCATION: (6)..(6)
<223> OTHER INFORMATION: n is a, c, g, or t -continued

```
<220> FEATURE:
<221> NAME/KEY: misc_feature
<222> LOCATION: (12)..(12)
<223> OTHER INFORMATION: n is a, c, g, or t

<400> SEQUENCE: 30
gtccanacca tnacrtaraa                                           20

<210> SEQ ID NO 31
<211> LENGTH: 7
<212> TYPE: PRT
<213> ORGANISM: Lawsonia intracellularis

<400> SEQUENCE: 31

Pro Phe Tyr Val Met Val Trp
1               5

<210> SEQ ID NO 32
<211> LENGTH: 8
<212> TYPE: PRT
<213> ORGANISM: Lawsonia intracellularis

<400> SEQUENCE: 32

Ser Asp Leu Glu Ile Phe Gly Arg
1               5
```